US012213660B2

(12) United States Patent
Lombardo et al.

(10) Patent No.: US 12,213,660 B2
(45) Date of Patent: Feb. 4, 2025

(54) SUTURE ANCHOR DRIVER

(71) Applicant: Conmed Corporation, Utica, NY (US)

(72) Inventors: Giuseppe Lombardo, New Port Richey, FL (US); Grady Breslich, St. Petersburg, FL (US); Matthew C. Summitt, Palm Harbor, FL (US); Gregory A. Alfonso, Seffner, FL (US); Robert A. Thibodeau, St. Petersburg, FL (US)

(73) Assignee: Conmed Corporation, Utica, NY (US)

( * ) Notice: Subject to any disclaimer, the term of this patent is extended or adjusted under 35 U.S.C. 154(b) by 994 days.

(21) Appl. No.: 16/982,352

(22) PCT Filed: Oct. 19, 2018

(86) PCT No.: PCT/US2018/056635
§ 371 (c)(1),
(2) Date: Sep. 18, 2020

(87) PCT Pub. No.: WO2019/182645
PCT Pub. Date: Sep. 26, 2019

(65) Prior Publication Data
US 2021/0007731 A1    Jan. 14, 2021

Related U.S. Application Data (60) Provisional application No. 62/648,034, filed on Mar. 26, 2018, provisional application No. 62/646,954, (Continued)

(51) Int. Cl.
*A61B 17/04*    (2006.01)

(52) U.S. Cl.
CPC .. *A61B 17/0401* (2013.01); *A61B 2017/0409* (2013.01); *A61B 2017/0462* (2013.01)

(58) Field of Classification Search
CPC ............... A61B 17/04; A61B 17/0401; A61B 2017/0409; A61B 2017/0462
See application file for complete search history.

(56) References Cited

U.S. PATENT DOCUMENTS 6,471,715 B1    10/2002  Weiss
6,780,198 B1    8/2004   Gregoire et al.
(Continued)

FOREIGN PATENT DOCUMENTS

EP    2446831       4/2013
JP    1990-193656 A2    7/1990
(Continued)

OTHER PUBLICATIONS

Examination Report No. 1, Application No. 2021254520, dated Feb. 27, 2023, pp. 1-3.
(Continued)

*Primary Examiner* — Mohamed G Gabr
(74) *Attorney, Agent, or Firm* — Bond, Schoeneck & King, PLLC; Frederick J. M. Price (57) ABSTRACT

A suture anchor driver with a tensioning mechanism. The suture anchor driver has a handle with a proximal end and a distal end. The handle has a recess with a shaft extending centrally therefrom. The suture anchor driver has a detent ring and a spool. The detent ring has a central aperture and one or more projections. The spool has a central aperture and is rotatable between first and second configurations. The spool has a plurality of protrusions extending from its side. The shaft extends through the central apertures in the detent ring and spool such that the projections of the detent ring are adjacent the protrusions extending from the spool. In the first configuration, one of the projections extends between two of the protrusions. In the second configuration, one of the projections is aligned with one of the protrusions.

15 Claims, 12 Drawing Sheets

Related U.S. Application Data filed on Mar. 23, 2018, provisional application No. 62/647,255, filed on Mar. 23, 2018.

(56) References Cited

U.S. PATENT DOCUMENTS

| | | |
|---|---|---|
| 6,951,565 B2 | 10/2005 | Keane et al. |
| 7,645,293 B2 | 1/2010 | Martinek et al. |
| 7,862,582 B2 | 1/2011 | Ortiz et al. |
| 7,875,042 B2 | 1/2011 | Martin et al. |
| 7,931,670 B2 | 4/2011 | Fiehler et al. |
| 7,963,972 B2 | 6/2011 | Foerster et al. |
| 8,052,696 B2 | 11/2011 | Del Rio et al. |
| 8,133,258 B2 | 3/2012 | Foerster et al. |
| 8,317,829 B2 | 11/2012 | Foerster et al. |
| 8,435,262 B2 | 5/2013 | Ortiz et al. |
| 8,679,159 B2 | 3/2014 | Sojka et al. |
| 8,828,029 B2 | 9/2014 | White et al. |
| 8,968,335 B2 | 3/2015 | Robinson et al. |
| 9,186,133 B2 | 11/2015 | Gregoire et al. |
| 9,370,351 B2 | 6/2016 | Sojka et al. |
| 9,451,954 B2 | 9/2016 | Moore et al. |
| 9,510,820 B2 | 12/2016 | Hernandez et al. |
| 9,717,492 B2 | 8/2017 | Sojka et al. |
| 9,750,493 B2 | 9/2017 | Robinson et al. |
| 10,702,258 B2 | 7/2020 | Moore et al. |
| 2003/0204193 A1 | 10/2003 | Gabriel et al. |
| 2005/0033364 A1 | 2/2005 | Gregoire et al. |
| 2005/0131430 A1 | 6/2005 | Ravikumar |
| 2006/0271060 A1 | 11/2006 | Gordon |
| 2007/0168014 A1* | 7/2007 | Jimenez .................... A61F 2/95 623/1.12 |
| 2016/0066901 A1 | 3/2016 | Gregoire et al. |

FOREIGN PATENT DOCUMENTS

| | | |
|---|---|---|
| JP | 2005-523103 A2 | 8/2005 |
| JP | 2012-179374 A2 | 9/2012 |
| JP | 2017-080428 A2 | 5/2017 |
| WO | 2010/014821 | 2/2010 |
| WO | 2012/170601 | 12/2012 |

OTHER PUBLICATIONS

International Search Report Form PCT/ISA/220, International Application No. PCT/US2018/056635, pp. 1-15, Dated Jan. 9, 2019.
Translated Japanese Office Action, Application No. 2022-079124, dated Mar. 29, 2023, pp. 1-11.

* cited by examiner

SUTURE ANCHOR DRIVER

CROSS-REFERENCES TO RELATED APPLICATIONS

This application is a National Stage Application under 35 U.S.C. 371 based on international patent application PCT/US18/56635 filed on Oct. 19, 2018, which claims priority to U.S. Provisional Patent Application Ser. No. 62/646,954, filed on Mar. 23, 2018, U.S. Provisional Patent Application Ser. No. 62/647,255, filed on Mar. 23, 2018 and U.S. Provisional Patent Application Ser. No. 62/648,034, filed on Mar. 26, 2018 the entireties of which are incorporated herein by reference.

BACKGROUND OF THE INVENTION

1. Field of the Invention

The present disclosure is directed generally to a suture anchor device for soft tissue to bone repair procedures and, more particularly, to a suture anchor driver with a tensioning mechanism.

2. Description of Related Art

Suture anchors are commonly used to repair soft tissue to bone in surgical procedures. Typically, the suture anchor is first inserted into a pre-formed hole with a driver. Then, the sutures are removed from the driver by pulling them from retaining cleats. In many suture anchor drivers, uncleating the suture and needles after inserting an anchor is an additional step that requires extra time during a procedure. In the case of deployable anchors, such as all-suture anchors, traction must be applied to the suture limbs to form the anchor into its final shape and secure it in the bone hole. Currently, the steps of removing the driver, releasing the sutures, and tractioning the anchor are executed separately, which results in lower surgeon efficiency and increased fatigue.

Therefore, there is a need for a simple to use suture anchor driver which has a tensioning mechanism to force a deployable anchor into its final shape and automatically release the suture from the handle.

SUMMARY OF THE INVENTION

Embodiments of the present invention are directed to a suture anchor driver. According to one aspect, the suture anchor driver has a handle with a proximal end and a distal end. The handle has a recess with a shaft extending centrally therefrom. The suture anchor driver has a detent ring and a spool. The detent ring has a central aperture and one or more projections. The spool has a central aperture and is rotatable between a first configuration and a second configuration. The spool has a first side and a second side. The second side has a plurality of protrusions extending therefrom. The shaft in the recess extends through the central apertures in the detent ring and the spool such that the projections of the detent ring are adjacent the plurality of protrusions extending from the spool. In the first configuration, one of the one or more projections extends between two of the plurality of protrusions. In the second configuration, one of the one or more projections is aligned with one of the plurality of protrusions.

According to another aspect, the suture anchor driver has a handle with a proximal end, a distal end, and a locking arm with a pawl extending therefrom. The handle has a recess with a barrier member extending thereacross. The recess is configured to retain a spool having a first surface and a second surface. The spool has first and second channels, which are at least partially separated between the first and second surfaces. A plurality of teeth extend radially from the second surface of the spool. The second channel of the spool has a recess configured to store needles connected to a length of suture. In a first configuration, the pawl of the locking arm extends between two of the plurality of teeth. In a second configuration, the locking arm is displaced such that the pawl is above the plurality of teeth. The spool is not rotatable in the first configuration and is rotatable in the second configuration.

In accordance with some embodiments described herein, a suture can release/unwind from a spool (which can spin with respect to a static detent ring, for example) in a handle of a suture anchor driver or anchor deployment device, but the spool needs to overcome a force imparted by a tensioning mechanism—teeth of a spool impacting and deflecting the finger like or other projections on the static detent ring—prior to being able to rotate (as an example), and in turn imparts a tensioning force on a suture (wrapped around the spool and extending through the slot on the handle) and to an attached anchor (when anchor is fixed, at least somewhat, in the bone hole). After the anchor is set/deployed in a bone hole, if the anchor is a soft anchor, this force can be tuned, predetermined and/or configured/utilized to set a soft anchor and/or test the setting/deployment of a soft anchor. Further, the force can be used to test the setting/deployment of a hard anchor. The force used to overcome the force imparted by the tensioning mechanism, and to rotate the spool to deploy/set and/or test is imparted by a user by pulling the handle away from the bone hole/deployment site. The force imparted by the tensioning mechanism can be increased/decreased in a number of ways including by changing the thickness, density and/or length of the finger like projections (or of the teeth), for example, as should be appreciated by a person of skill in the art in conjunction with a review of this disclosure.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
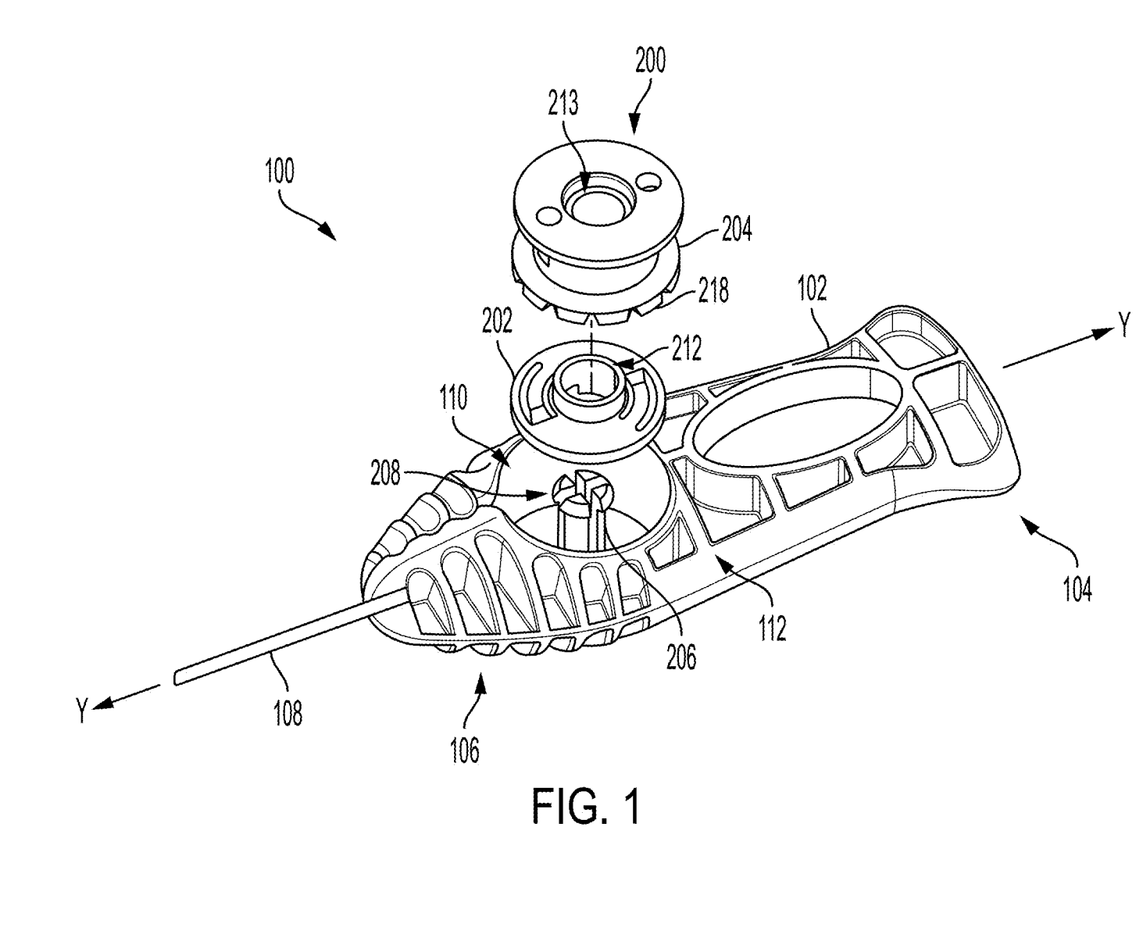
FIG. 1 is a partial exploded perspective view schematic representation of a suture anchor driver, according to an embodiment.

Referring now to the figures, wherein like reference numerals refer to like parts throughout, FIG. 1 shows a perspective view schematic representation of a suture anchor driver 100, according to an embodiment. The suture anchor driver 100 comprises a handle 102. The handle 102 extends from a proximal end 104 to a distal end 106 along a central longitudinal y-y axis. The handle 102 can be any shape, such as cylindrical or rectangular, for example. As shown in the depicted embodiment, the handle 102 is ergonomically designed such that the handle 102 is configured to fit within the hand of the user. The handle 102 can be composed of plastic or any other suitable material (as should be understood by a person of skill in the art in conjunction with a review of this disclosure).

Figure 2:
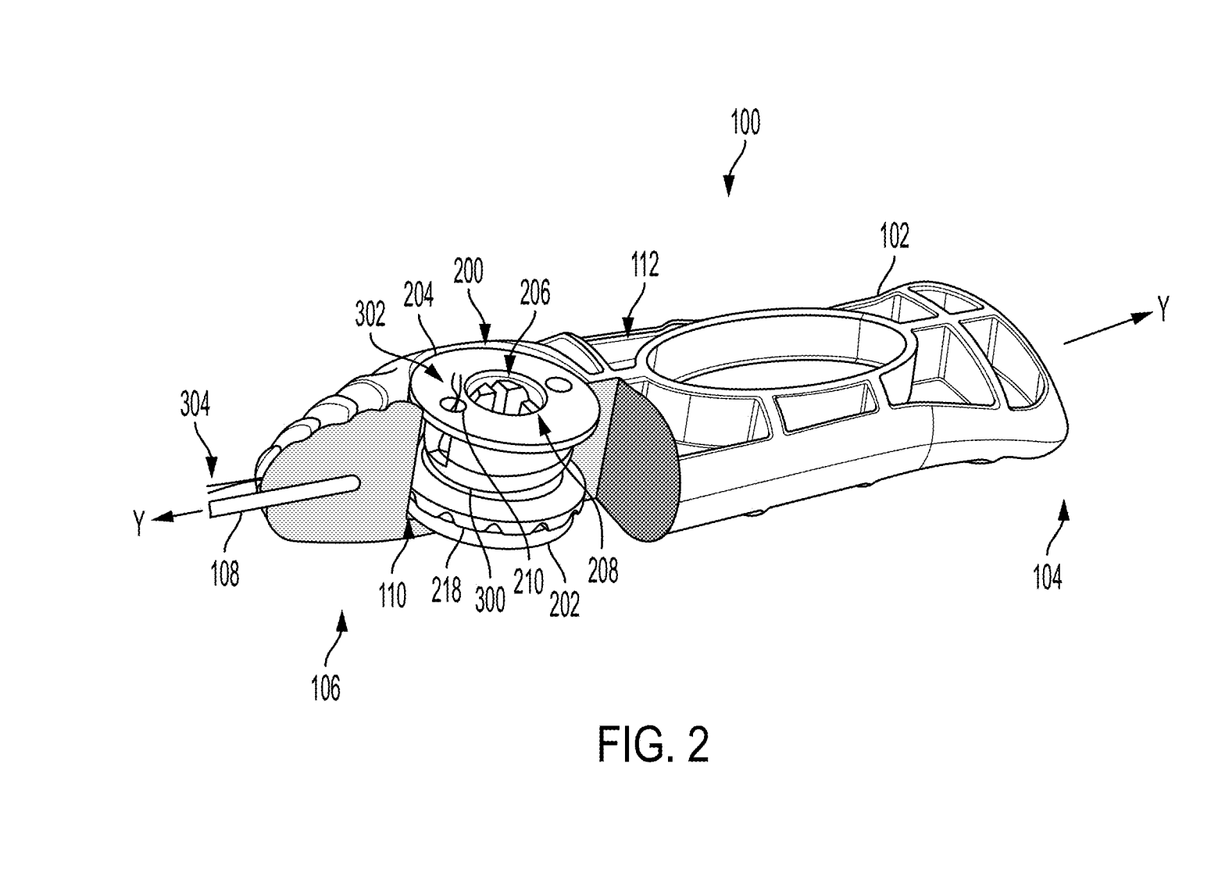
FIG. 2 is a partial cutaway bottom view schematic representation of the suture anchor driver, according to an embodiment.

Turning now to FIG. 2, there is shown a partial cutaway bottom view schematic representation of the suture anchor driver 100, according to an embodiment. The anchor driver 100 shown in FIG. 1 also comprises a driver 108 extending into the distal end 106 of the handle 102. The driver 108 may be composed of metal, such as stainless steel, or any other suitable material (as should be understood by a person of skill in the art in conjunction with a review of this disclosure). In the depicted embodiment, the driver 108 extends distally from the distal end 106 along the central longitudinal y-y axis.

As shown in FIGS. 1 and 2, the anchor driver 100 further comprises a tensioning mechanism 200. The tensioning mechanism 200 comprises a detent ring 202, a spool 204, and a shaft 206, as shown in FIG. 1. In the embodiment shown in FIG. 1, the handle 102 comprises a recess 110 sized and configured to retain the detent ring 202 and spool 204 axially therein. The shaft 206 is centrally located within the recess 110 and extends from the recess 100 to a first side 112 of the handle 102. In the depicted embodiment, the shaft 206 does not (but can) extend past the first side 112 of the handle 102. Further, as shown in FIGS. 1 and 2, the shaft 206 has a pronged end 208 such that the detent ring 202 and spool 204 can be removably installed around the shaft 206 within the recess 110. The pronged end 208 maintains the detent ring 202 and spool 204 within the recess 110, but when the prongs of the pronged end 208 are moved toward each other, the detent ring 202 and spool 204 can be removed from the recess 110.

Still referring to FIG. 2, the detent ring 202 is positioned within the recess 110 around the shaft 206. The spool 204 is then positioned within the recess 110 around the shaft 206 and on the detent ring 202 such that the spool 204 extends to the first side 112 of the handle 102. Prior to inserting the spool 204 into the recess 110, suture 300 (connected to a suture anchor (not shown)) is wrapped around the spool 204. The suture anchor (not shown) may be any anchor, such as an all-suture or "soft" anchor shown and described in U.S. Pat. No. 9,826,971, the contents of which are hereby incorporated by reference herein in their entirety.

As a brief background, suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652, the contents of which are hereby incorporated by reference herein in their entirety) and a suture or filament portion.

Methods and devices for inserting/deploying such all-suture anchors are known, examples of which are disclosed in U.S. Pat. No. 9,173,652.

As described in U.S. Pat. No. 8,409,252, for example (the contents of which are hereby incorporated by reference herein in their entirety), "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

As shown in FIG. 2, a first end 302 of the suture 300 can be pulled through an aperture 210 within the spool 204 to prevent the suture 300 from unraveling as it is wound around the spool 204. In another embodiment, the spool 204 can have any conventional slot, hook, or connector to secure the first end 302 of the suture 300. The suture 300 extends from the spool 204 such that a second end 304 of the suture 300 extends distally from the handle 102 near the driver 108, as shown in FIG. 2. In an embodiment shown in FIG. 10, the handle 102 comprises a slot 114 or other aperture extending from the recess 110 to a location on the handle 102 adjacent the driver 102.

Figure 3:
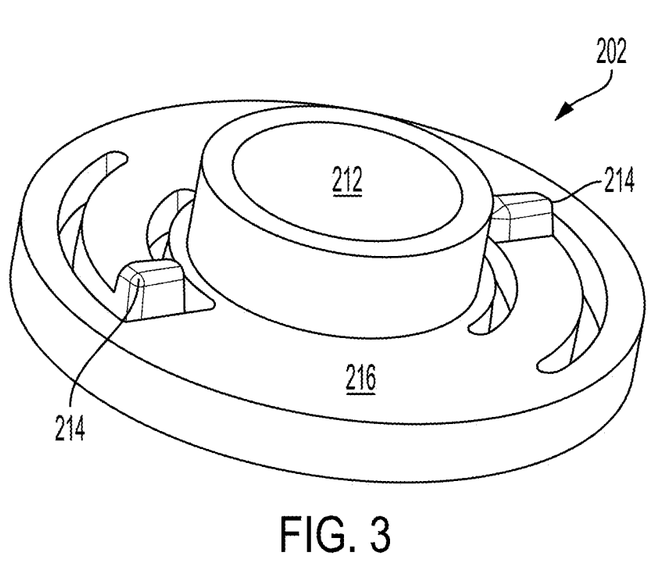
FIG. 3 is a perspective view schematic representation of the detent ring of the tensioning mechanism of the suture anchor driver, according to an embodiment.

Referring now to FIG. 3, there is shown a perspective view schematic representation of the detent ring 202 of the tensioning mechanism 200 of the suture anchor driver 100, according to an embodiment. In the depicted embodiment, the detent ring 202 comprises a central aperture 212 to accommodate the shaft 206 of the tensioning mechanism 200 when the detent ring 202 is placed within the recess 110 of the handle 102. The detent ring 202 also comprises one or more finger-like projections 214 extending from a surface 216 of the detent ring 202. The finger-like projections 214 engage the spool 204 as described below.

Turning back to FIGS. 1-2, the spool 204 similarly comprises a central aperture 213 for accommodating the shaft 206 within the recess 110 of the handle 102. The spool 204 also comprises a plurality of ridges, teeth, or other protrusions 218 extending therefrom. The teeth 218 extend from the spool 204 toward the surface 216 of the detent ring 202. When the detent ring 202 and spool 204 are installed within the recess 110, the finger-like projections 214 of the detent ring 202 are adjacent the teeth 218 of the spool 204.

Figure 4:
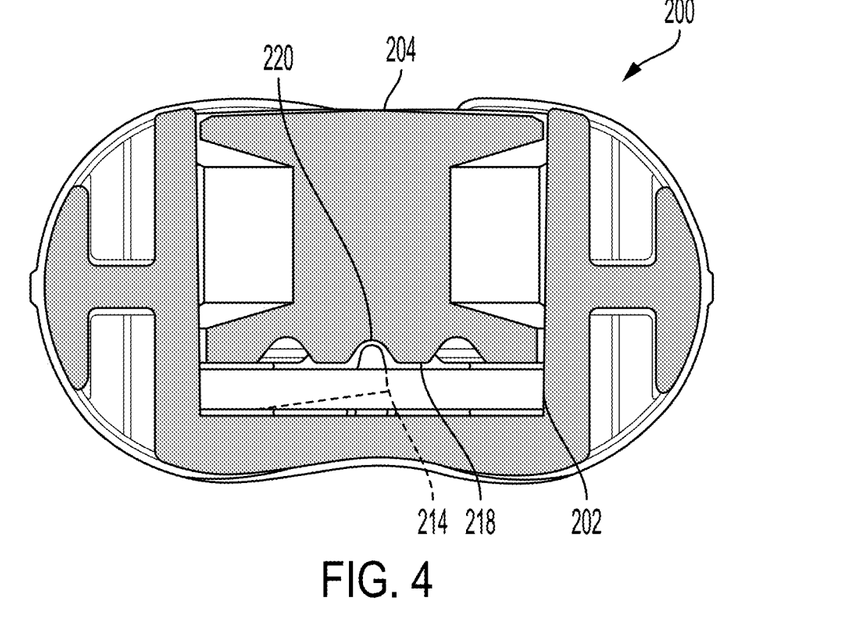
FIG. 4 is a cutaway side view schematic representation of the spool and detent ring in a first configuration, according to an embodiment.
Figure 5:
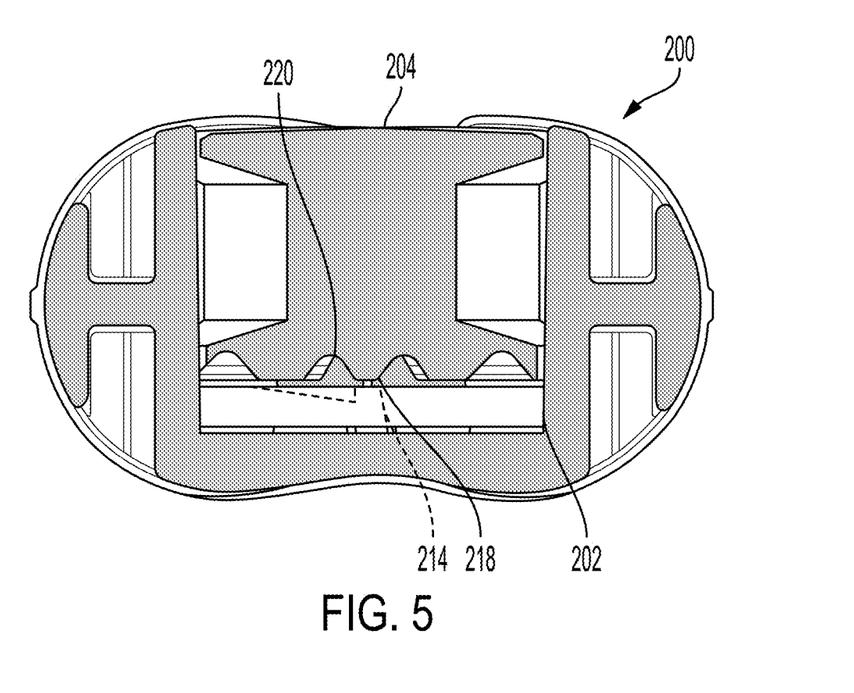
FIG. 5 is a cutaway side view schematic representation of the spool and detent ring in a second configuration, according to an embodiment.

Referring now to FIGS. 4 and 5, there are shown cutaway side views schematic representations of the spool 204 and detent ring 202 in a first configuration and second configuration, respectively, according to an embodiment. In a first configuration, a projection 214 of the detent ring 202 is within a gap 220 between two teeth 218 of the spool 204, as shown in FIG. 4. To move the tensioning mechanism 200 to a second configuration, the spool 204 is rotated. The spool 204 is rotated when traction is applied to the suture 300. The traction on the suture 300 imparts torque on the spool 204 causing it to rotate.

The spool 204 resists rotation because the projections 214 of the detent ring 202 extending in the gap 220 between the teeth 218 of the spool 204 or catch on the teeth 218 of the spool 204. The resistance to the rotation applies force to the anchor (not shown) attached to the suture 300. The force causes a deployable suture anchor (not shown) to expand or otherwise form toward its final shape. Force is applied to the suture anchor (not shown) until the projection 214 of the detent ring 202 overcomes the resistance or traction and is moved from the gap 220 between the teeth 218 into alignment with one of the plurality of teeth 218, as shown in FIG. 5. Additional tension on the suture 300 causes the projection 214 of the detent ring 202 to move into an adjacent gap 220 where the spool 204 against resists rotation. As described above, the resistance applies force to the suture anchor (not shown) causing it to deploy or form to its final shape. Thus, tension can be selectively applied to the suture anchor (not shown) through a selected number of rotations of the spool 204.

Figure 6:
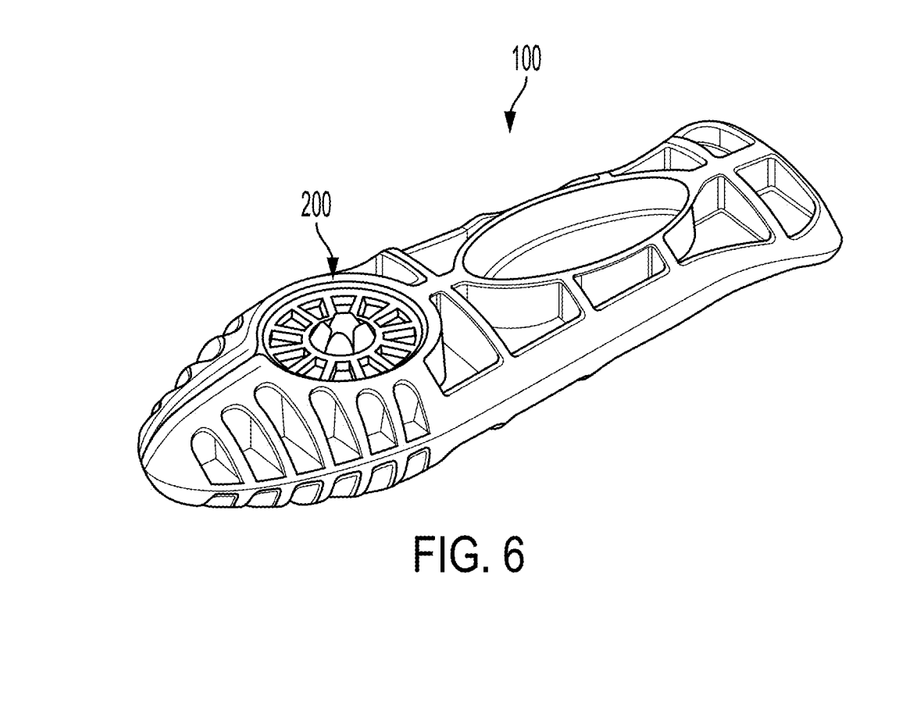
FIG. 6 is a perspective view schematic representation of a suture anchor driver, according to an alternative embodiment.
Figure 7:
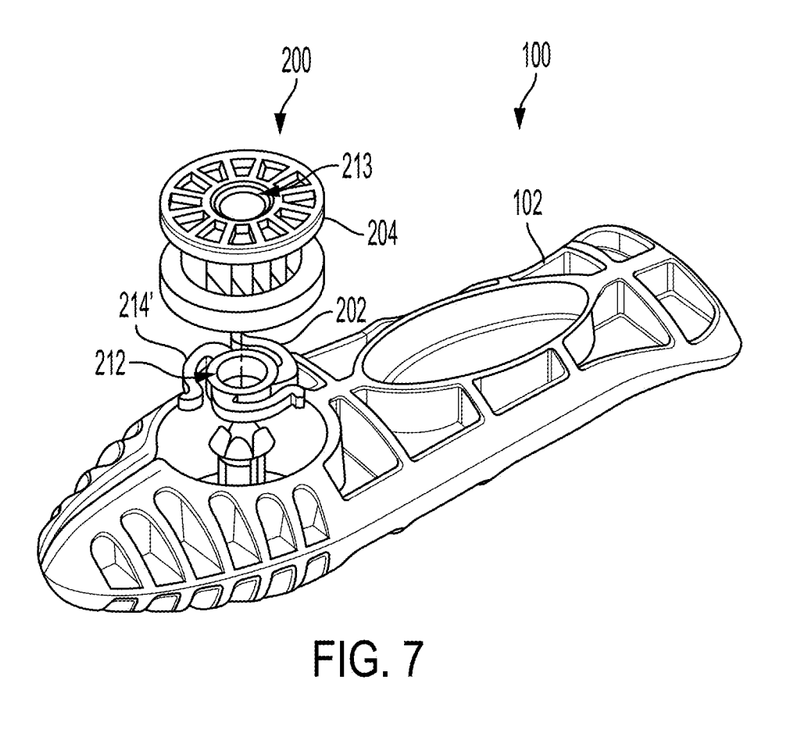
FIG. 7 is a partial exploded perspective view schematic representation of a suture anchor driver, according to an alternative embodiment.

Turning now to FIGS. 6 and 7, there are shown perspective and partial exploded perspective views schematic representations of a suture anchor driver 100, according to an alternative embodiment. In the depicted embodiment, the detent ring 202 of tensioning mechanism 200 of the anchor driver 100 comprises one or more arms 214' instead of the projections 214 shown in the embodiment of FIGS. 1-2. In FIG. 7, the arms 214' extend from radially, whereas in FIGS. 1-2, the projections 214 extend up from the surface 216 of the detent ring 202 toward the first side 112 of the handle 102. To accommodate the radial arms 214', the embodiment of the spool 204 in FIGS. 6-7 comprises radial ridges, teeth, or other protrusions 218' which extend inward toward the central aperture 213 in the spool 204.

Figure 8:
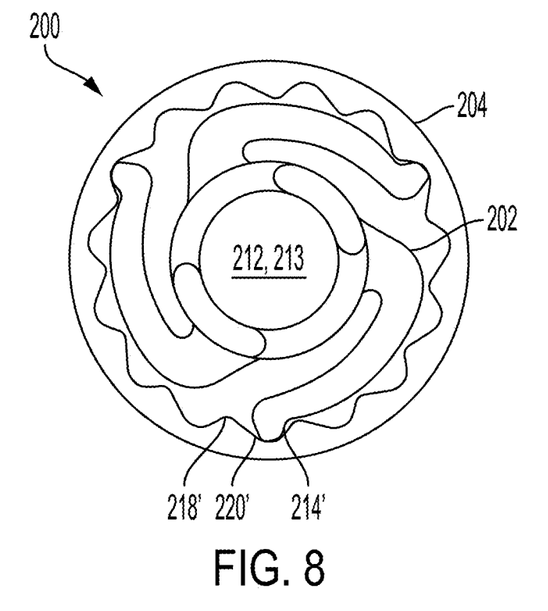
FIG. 8 is a side view schematic representation of the detent ring and spool of the anchor driver in a first configuration, according to an alternative embodiment.
Figure 9:
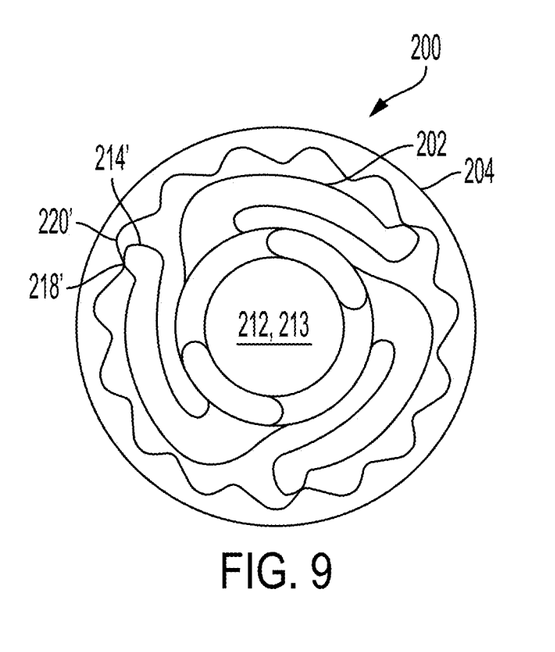
FIG. 9 is a side view schematic representation of the detent ring and spool of the anchor driver in a second configuration, according to an alternative embodiment.
Figure 10:
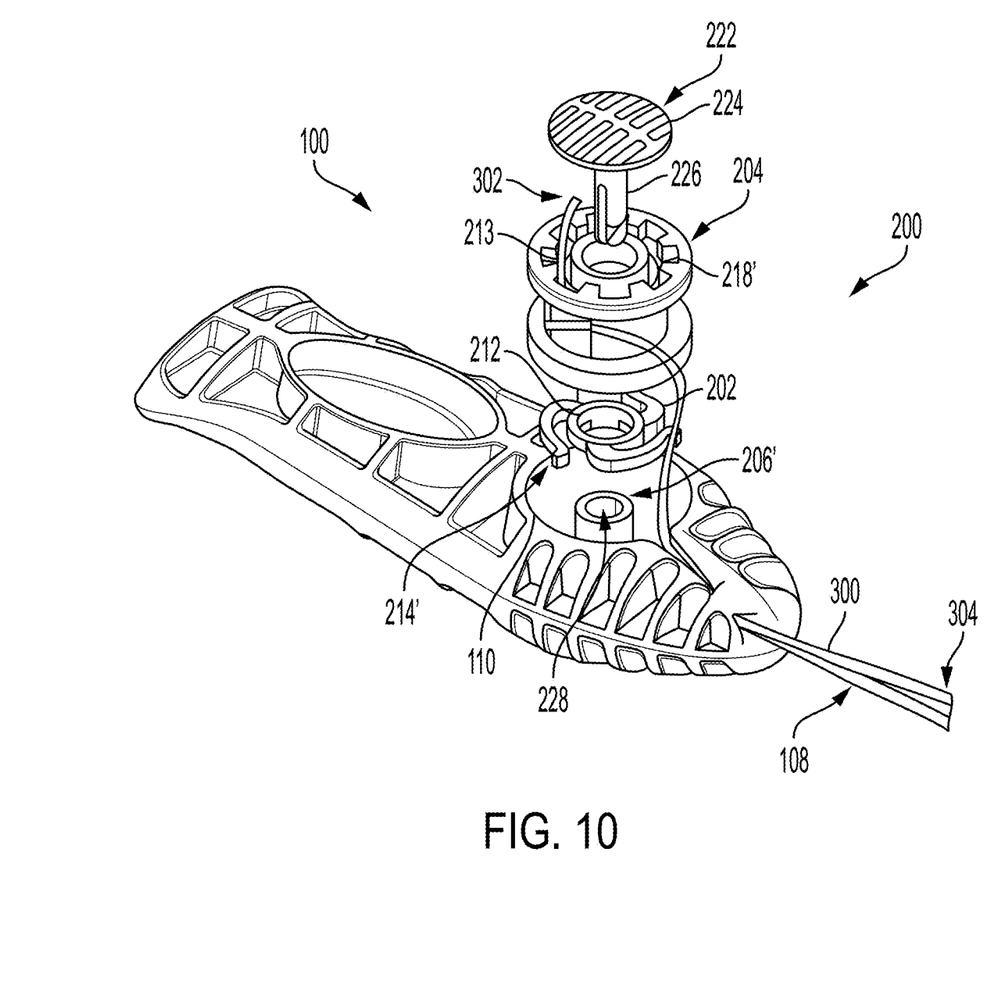
FIG. 10 is a partial exploded perspective view of a suture anchor driver, according to another alternative embodiment.

Referring now to FIGS. 8 and 9, there are shown side views schematic representations of the detent ring 202 and spool 204 of the anchor driver 100 in a first configuration and a second configuration, respectively, according to an alternative embodiment (which can apply to and substantially illustrate a portion of the alternative embodiment shown and described with respect to FIGS. 6-7 and FIG. 10). In a first configuration, an arm 214' of the detent ring 202 is within a gap 220' between the teeth 218' of the spool 204, as shown in FIG. 8. To move the tensioning mechanism 200 to a second configuration, the spool 204 is rotated by traction applied to the suture 300. As described above, the spool 204 resists rotation, applying force to the suture anchor (not shown) and partially deploying it. The spool 204 resists rotation until the arm 214' of the detent ring 202 is finally moved from the gap 220' between the teeth 218' into alignment with a tooth 218', as shown in FIG. 9. As described above, each continued rotation of the spool 204 applies additional force to the suture 300 and the suture anchor (not shown), deploying the suture anchor (not shown).

Turning now to FIG. 10, there is shown a partial exploded perspective view schematic representation of a suture anchor driver 100, according to another alternative embodiment. Like the embodiment shown in FIGS. 6-9, the anchor driver 100 in FIG. 10 has a detent ring 202 with arms 214' extending radially therefrom. The radial arms 214' engage radial ridges, teeth, or other protrusions 218' of the spool 204, as shown in FIG. 10. However, in the embodiment shown in FIG. 10, the shaft 206' of the tensioning mechanism 200 does not have a pronged end 208 (as shown in FIG. 1). In the depicted embodiment, the shaft 206' is a rigid tube, cylindrical in shape. To maintain the detent ring 202 and the spool 204 within the recess 110 of the handle 102, the tensioning mechanism 200 additionally comprises a fastener 222. In the depicted embodiment, the fastener 222 is a cap 224 with a stem 226 extending centrally therefrom. In use, the stem 226 of the fastener 222 is placed through the apertures 213, 212 in the spool 204 and the detent ring 202, and through an inner channel 228 within the tubular shaft 206'.

Figure 11:
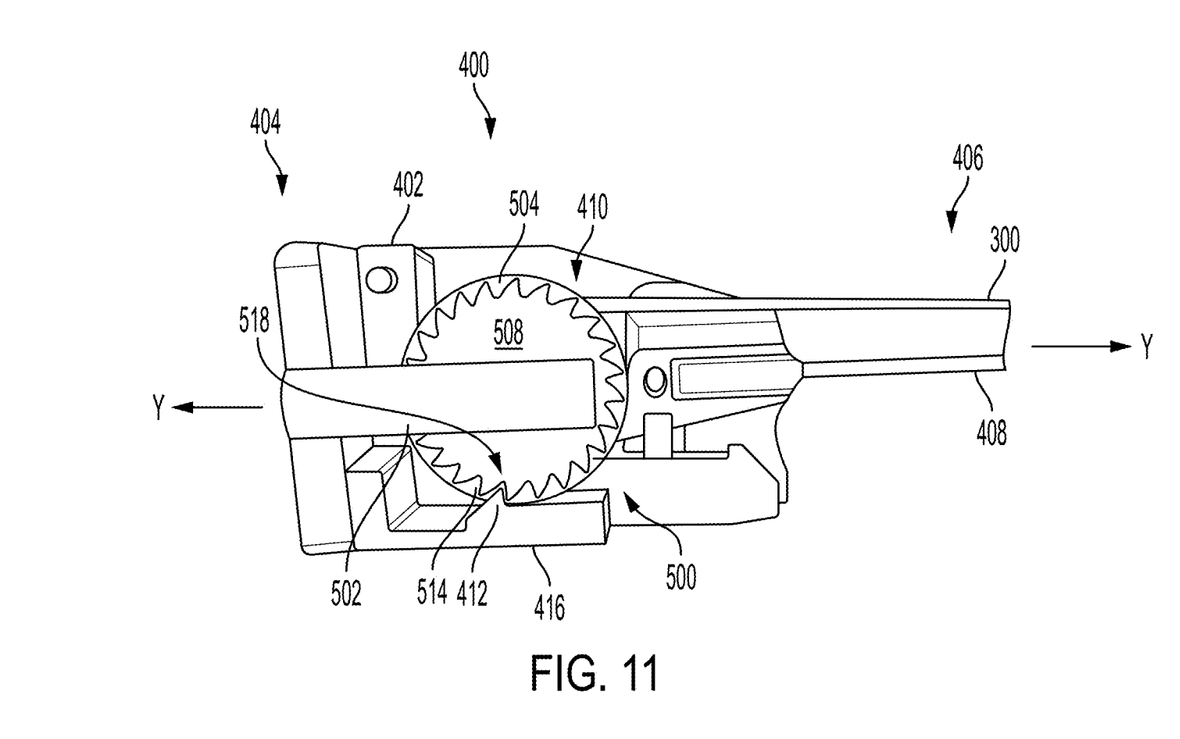
FIG. 11 is a side view schematic representations of a suture anchor driver in a first configuration, according to yet another alternative embodiment.
Figure 12:
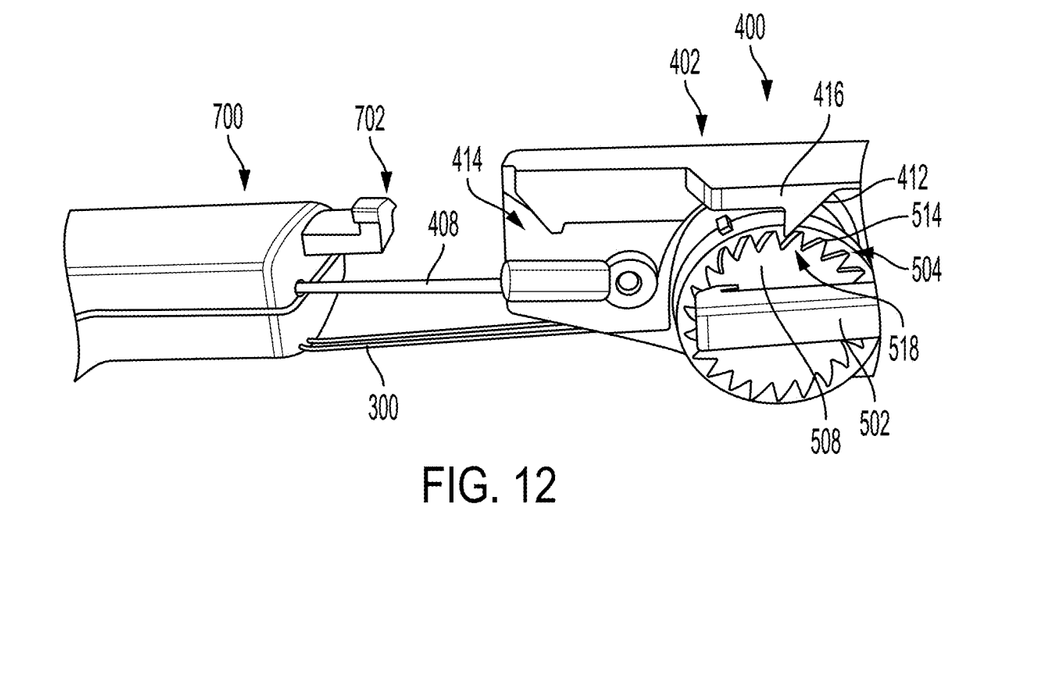
FIG. 12 is a side view schematic representations of a driver of the suture anchor driver inserted into a guide, according to yet another alternative embodiment.
Figure 13:
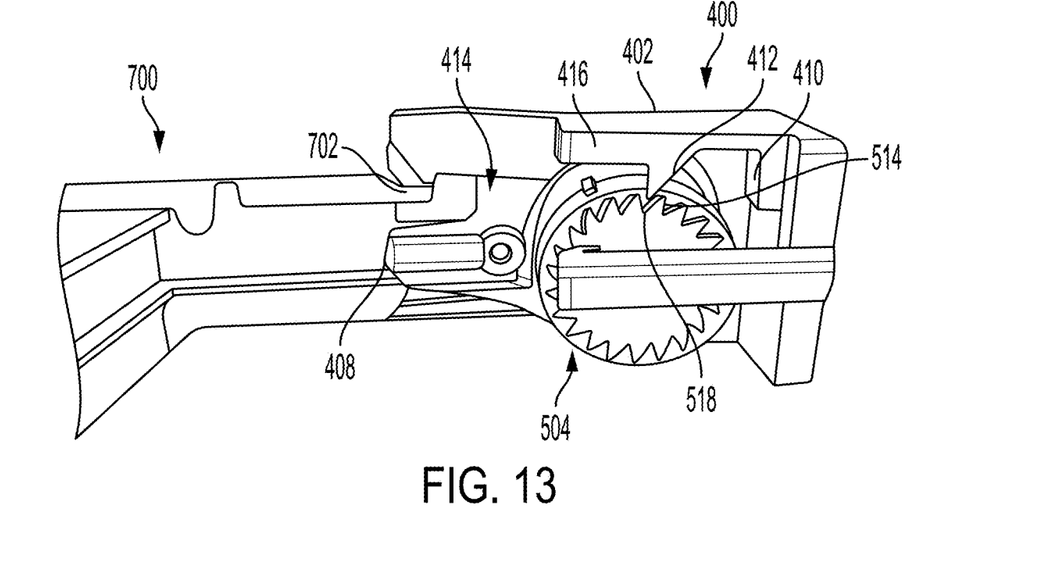
FIG. 13 is a side view schematic representations of the suture anchor driver in a second configuration, according to yet another alternative embodiment.

Referring now to FIGS. 11-13, there are shown side views schematic representations of a suture anchor driver 400 between first and second configurations, according to yet another alternative embodiment. In the embodiment shown in FIGS. 11-13, the anchor driver 400 comprises a handle 402 extending from a proximal end 404 to a distal end 406 along a central longitudinal y-y axis. The handle 402 can be any shape, composed of plastic or any other suitable material, and ergonomically designed to fit within the hand of the user (as described above in conjunction with the embodiments shown in FIGS. 1-10). The anchor driver 400 shown in FIG. 11 also comprises a driver 408 extending into the distal end 406 of the handle 402. The driver 408 may be composed of metal (or any other suitable material) and extends distally from the distal end 406 along the central longitudinal y-y axis. As shown in FIG. 11, the handle 402 comprises a recess 410 to receive a spool 504 of a tensioning mechanism 500. In the depicted embodiment, the spool 504 slides into the recess 410 and is held within the recess 410 by a barrier member 502 of the tensioning mechanism 500, such as an arm or rod of the handle 402.

Figure 14:
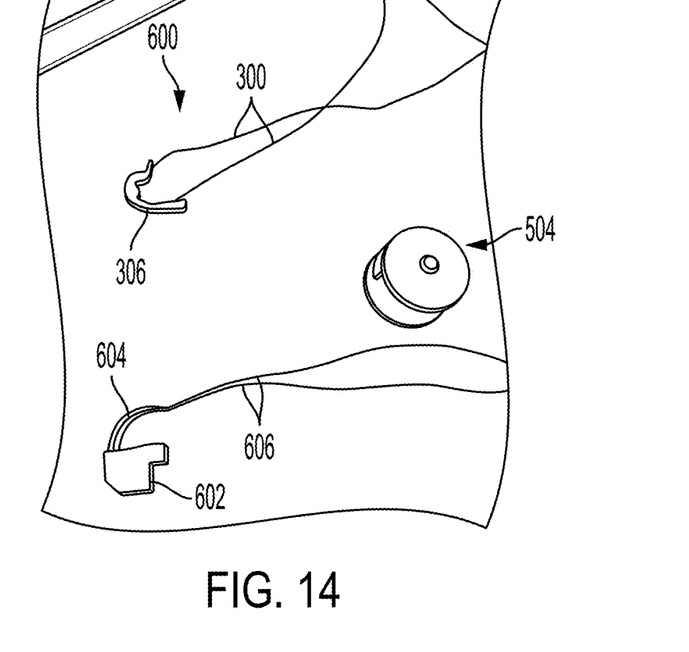
FIG. 14 is a perspective view schematic representation of the spool and suture components of the suture anchor driver, according to yet another alternative embodiment.

Turning briefly to FIGS. 14-17, there are shown various views of a spool 504 and suture components 600, according to yet another alternative embodiment. FIG. 14 shows a perspective view of the spool 504 and suture components 600 of the suture anchor driver 400. The suture components 600 include a foam block 602 with needles 604 embedded or otherwise hooked therein and a length of suture 606 attached to the needles 604. The suture components 600 also include a suture anchor 306 on a length of suture 300. In the depicted embodiment, the needles 604 are curved or hooked.

Figure 15:
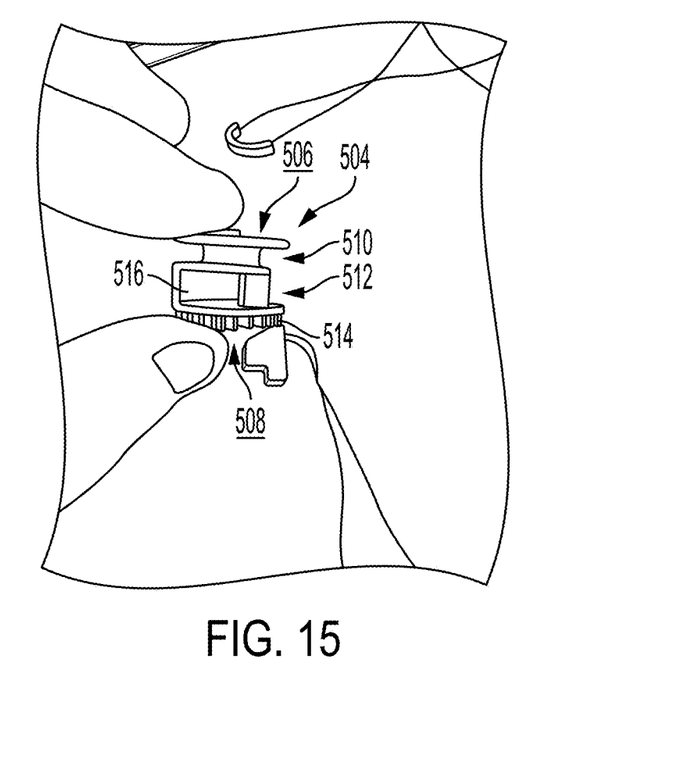
FIG. 15 is a top view schematic representation of the spool of the suture anchor driver, according to yet another alternative embodiment.
Figure 16:
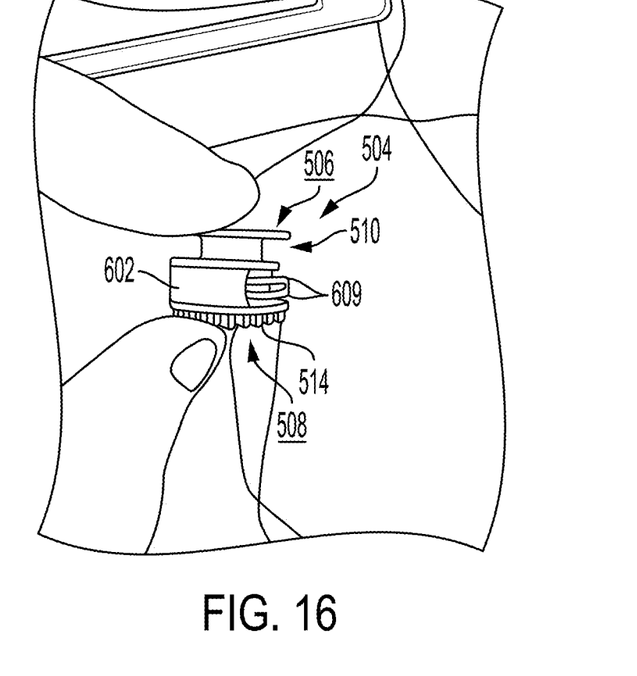
FIG. 16 is a top view schematic representation of the spool with the suture components loaded thereon, according to yet another alternative embodiment.

FIG. 15 shows an embodiment of the spool 504 with a first surface 506 and a second surface 508 with at least partially separated first and second channels 510, 512 therebetween. As shown in both FIGS. 15 and 16 (and FIG. 11), the second surface 508 of the spool 504 comprises a plurality of radially extending teeth 514. The second channel 512 of the spool 504 comprises a recess 516 configured to accommodate or otherwise house the foam block 602, as shown in FIG. 16.

Figure 17:
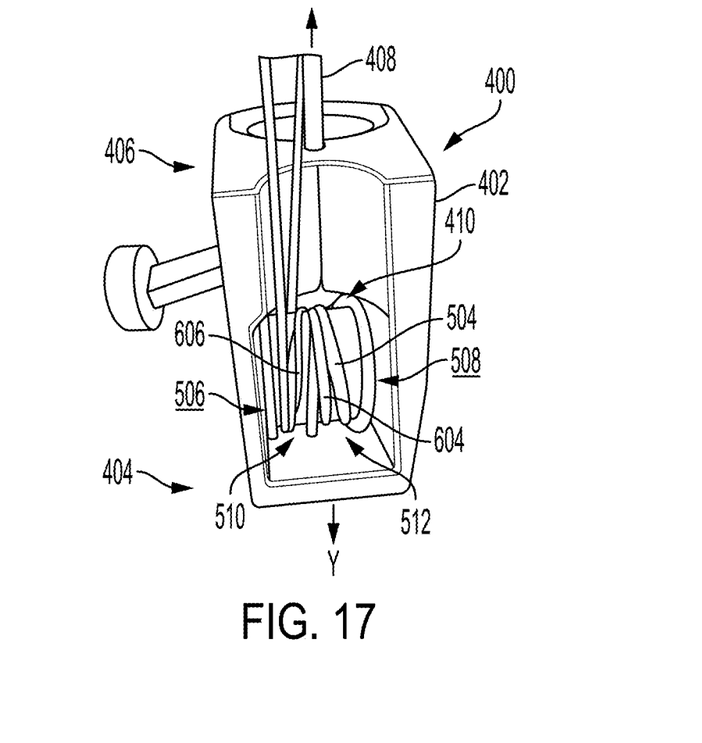
FIG. 17 is a top view schematic representation of the spool loaded into the suture anchor driver, according to yet another alternative embodiment.

As the needles 604 are curved or hooked, the needles 604 extend along the second channel 512 when the foam block 602 is inserted into the recess 516 of the spool 504. As shown in FIG. 17, the length of suture 606 attached to the needles 604 is wrapped around the first channel 510. After the length of suture 606 attached to the needles 604 is loaded on the spool 504, the spool 504 is placed within the recess 410 of the handle 402. As shown in FIG. 11, the spool 504 is placed within the recess 410 such that the second surface 508 and teeth 514 are adjacent the barrier member 502 of the handle 402. The suture anchor 306 (and attached suture 300) is also loaded on the driver 408.

Still referring to FIG. 11, the handle 402 additionally comprises a locking arm 416 with a pawl 412 or other similar protrusion extending into a gap 518 between the two of the plurality of teeth 514 of the spool 504 when the anchor driver 400 is in the first configuration. In the first configuration, the pawl 412 prevents the spool 504 from rotating within the recess 410 of the handle 402 so that the suture anchor 306 can be inserted with the suture 300 having a fixed tension. Specifically, the suture anchor 306 is inserted into a pre-formed hole (or bone hole) with tension on the suture 300, which is connected to the spool 504 in the handle 402. As the spool 504 cannot rotate, no slack (or reduction in tension) can be introduced to the suture 300. With fixed tension on the suture anchor 306, it is inserted into the bone hole by the driver 408 through a guide 700, as shown in FIG. 12.

Turning now to FIG. 13, there is shown a side view of the suture anchor driver 400 in the second configuration, according to yet another alternative embodiment. In the depicted embodiment, the driver 408 has been advanced as far as possible within the guide 700. The guide 700 comprises a feature 702 which enters a slot 414 within the handle 402 adjacent the locking arm 416 having the pawl 412. As the driver 408 extends as far as possible into the guide 700, the feature 702 of the guide 700 enters the slot 414 and deflects the locking arm 416 away from the spool 504. As the locking arm 416 is deflected away from the spool 504, the pawl 412 disengages the gap 518 between the teeth 514 of the spool 504. The spool 504 is then free to spin or otherwise rotate within the recess 410 of the handle 402. As the spool 504 can spin within the recess 410, the needles 604 and the attached length of suture 606, and the suture 300 (connected to the suture anchor 306) can be unspooled (i.e., removed) from the handle 402 to complete installation of the suture anchor 306.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture anchor driver, comprising:
a handle having a proximal end and a distal end;
a recess in the handle with a shaft extending centrally therefrom;
a detent ring with a central aperture, the detent ring having one or more projections;
a spool with a central aperture, the spool rotatable between a first configuration and a second configuration, the spool having a first side and a second side, the second side having a plurality of protrusions extending therefrom;
wherein the shaft extends through the central aperture in the detent ring and the central aperture of the spool such that the one or more projections of the detent ring are adjacent the plurality of protrusions extending from the spool, and wherein the shaft further comprises a pronged end; and
wherein in the first configuration, one of the one or more projections of the detent ring extends between two of the plurality of protrusions of the spool and in the second configuration, one of the one or more projections of the detent ring is aligned with one of the plurality of protrusions of the spool.

2. The suture anchor driver of claim 1, further comprising a driver extending from the distal end of the handle.

3. The suture anchor driver of claim 1, wherein the one or more projections extend from the detent ring toward the second side of the spool within the recess.

4. The suture anchor driver of claim 3, wherein the plurality of protrusions extend from the second side of the spool toward the detent ring within the recess.

5. The suture anchor driver of claim 1, wherein the one or more projections are arms which extend radially from the detent ring.

6. The suture anchor driver of claim 5, wherein the plurality of protrusions extend radially toward the central aperture of the spool.

7. The suture anchor driver of claim 1, wherein the recess extends to a first side of the handle.

8. The suture anchor driver of claim 1, further comprising a slot on an exterior of the handle, the slot extending into the recess.

9. The suture anchor driver of claim 8, wherein the slot is adjacent a driver extending from the distal end of the handle.

10. The suture anchor driver of claim 9, wherein the spool comprises an aperture on the first side configured to receive an end of the suture therethrough.

11. The suture anchor driver of claim 8, further comprising a suture wrapped around the spool and extending through the slot on the handle.

12. The suture anchor driver of claim 1, further comprising fastener having a cap with a stem extending centrally therefrom, the stem configured to extend into an inner channel of the shaft.

13. The suture anchor driver of claim 1, wherein at least one of the one or more projections of the detent ring is configured to move from between two of the plurality of the protrusions of the spool to an adjacent two of the plurality of the protrusions of the spool per an application of a predetermined force.

14. The suture anchor driver of claim 13, wherein the predetermined force is imparted to a suture wrapped around the spool and extending through the slot on the handle.

15. The suture anchor driver of claim 13, wherein the predetermined force is imparted to an anchor attached to the suture.

* * * * *